United States Patent
Biegun et al.

(10) Patent No.: US 10,231,848 B2
(45) Date of Patent: Mar. 19, 2019

(54) SAID IMPACTING DEVICE FOR IMPARTING AN IMPACT TO A STEM

(71) Applicant: XNOV IP, Luxembourg (LU)

(72) Inventors: Jean-François Biegun, Porrentruy (CH); Frédérique Biegun, Porrentruy (CH); Pascal Loehle, Porrentruy (CH)

(73) Assignee: XNOV IP, Luxembourg (LU)

( * ) Notice: Subject to any disclaimer, the term of this patent is extended or adjusted under 35 U.S.C. 154(b) by 128 days.

(21) Appl. No.: 15/254,634

(22) Filed: Sep. 1, 2016

(65) Prior Publication Data
US 2017/0056205 A1 Mar. 2, 2017

(30) Foreign Application Priority Data

Sep. 2, 2015 (FR) ...................................... 15 01817

(51) Int. Cl.
| | |
|---|---|
| A61F 2/46 | (2006.01) |
| A61B 90/00 | (2016.01) |
| A61F 2/34 | (2006.01) |
| A61B 17/92 | (2006.01) |
| A61F 2/30 | (2006.01) |

(52) U.S. Cl.
CPC ............ *A61F 2/4609* (2013.01); *A61B 17/92* (2013.01); *A61B 90/03* (2016.02); *A61F 2/34* (2013.01); *A61F 2/4637* (2013.01); *A61B 2090/034* (2016.02); *A61F 2002/30558* (2013.01); *A61F 2002/30566* (2013.01); *A61F 2002/4627* (2013.01); *A61F 2002/4681* (2013.01); *A61F 2310/00179* (2013.01)

(58) Field of Classification Search
CPC .............................. A61F 2/4609; A61B 17/92
See application file for complete search history.

(56) References Cited

U.S. PATENT DOCUMENTS

| | | | | | |
|---|---|---|---|---|---|
| 2,187,852 | A | * | 1/1940 | Friddle | A61B 17/742 227/147 |
| 4,263,903 | A | * | 4/1981 | Griggs | A61B 17/0642 227/147 |
| 2005/0251263 | A1 | | 11/2005 | Forrer et al. | |
| 2014/0142583 | A1 | * | 5/2014 | Fortin | A61B 17/1604 606/100 |

FOREIGN PATENT DOCUMENTS

| | | |
|---|---|---|
| EP | 1 190 687 A1 | 3/2002 |
| EP | 1 707 160 A1 | 10/2006 |
| EP | 2 732 776 A1 | 5/2014 |

OTHER PUBLICATIONS

French Search Report (FR 1501817) (2 pages—dated Jun. 28, 2016).

* cited by examiner

*Primary Examiner* — Christian Sevilla
(74) *Attorney, Agent, or Firm* — Renner, Kenner, Greive, Bobak, Taylor & Weber

(57) ABSTRACT

An impaction device (1) intended to impart a blow to a stem, the stem itself being coupled to an element forming an insert intended to be inserted into a receiving element, in particular a ceramic insert in a cup of a cotyloid cavity of a hip; the impaction device (1) including an element (4) forming a barrel defining a channel (5) or an internal chamber that has an opening via which at least part of the stem, in particular a proximal end segment of the stem, can be inserted; means of applying a blow intended to apply to the part of the stem introduced into the chamber a pre-determined blow force; and means (12, 14) for triggering the blow application means.

9 Claims, 4 Drawing Sheets

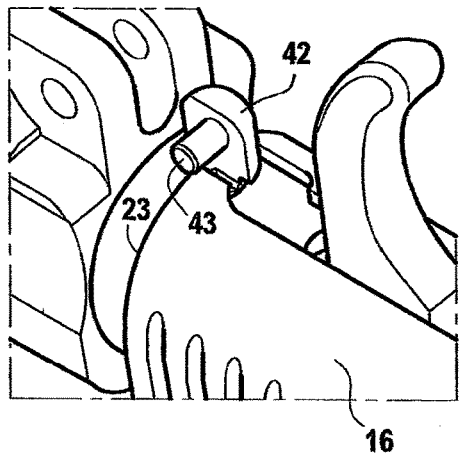 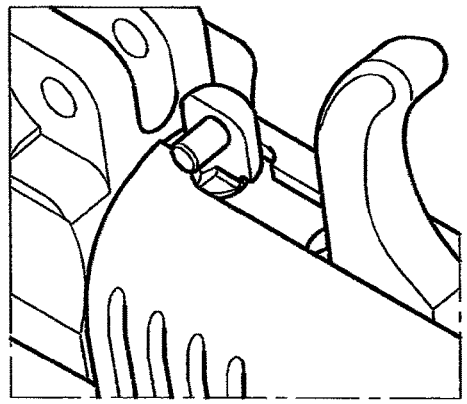
FIG.4a FIG.4b
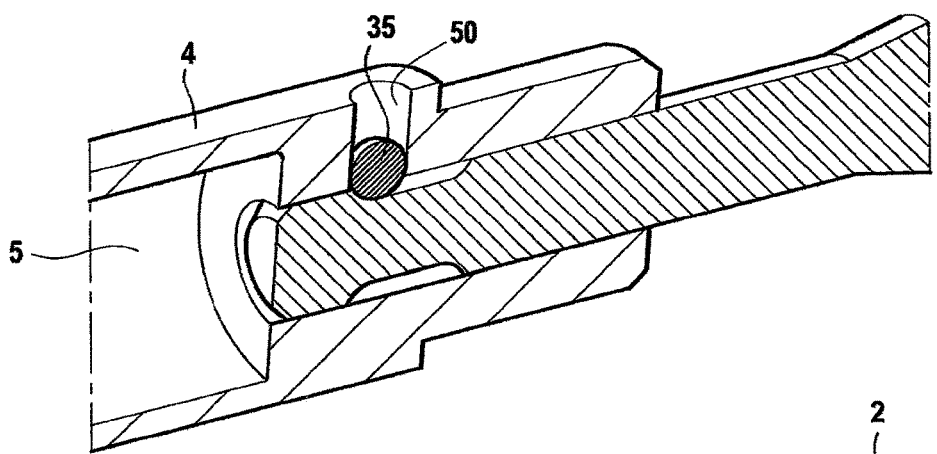
FIG.5a
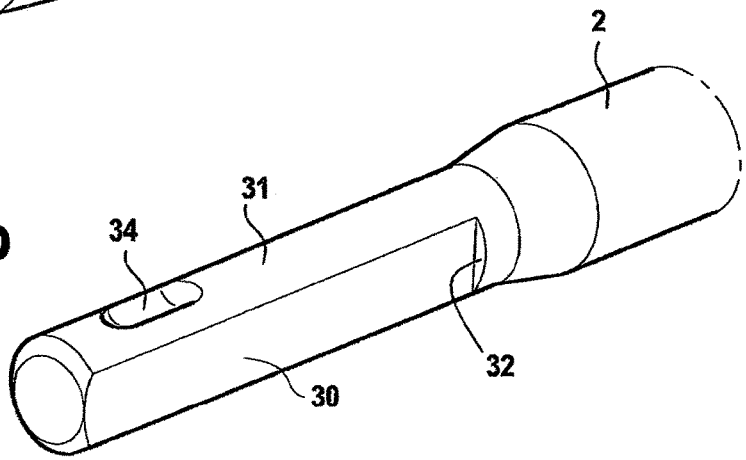
FIG.5b

SAID IMPACTING DEVICE FOR IMPARTING AN IMPACT TO A STEM

The present invention relates to a so-called impaction device intended to impart a blow to a stem, the purpose of the stem being to transmit this blow to an insert, for example an insert made of ceramic, in order to insert it into a receiving element, for example a cup intended to be positioned in the cotyloid cavity of a hip.

Nowadays, in known devices, in order to insert an insert into a cup intended to then be placed in the cotyloid cavity of a hip, the insert is grasped by means of a gripping device comprising a stem, the insert gripped by the gripping device is positioned above the open cavity of the cup and, with the aid of an impaction device in the form of a hammer, the surgeon applies a blow to the stem so as to make the insert penetrate into the cup.

These devices and methods from the prior art are imprecise and, in particular, it is often the case that the force applied by the blow is not of the correct value and/or it is not perfectly centered, and this brings about an insertion of the insert in the cup that is out of alignment and/or incomplete, obliging the surgeon most of the time to start again with a new insert and a new cup because the insert that has been incorrectly inserted into the cup can no longer be removed. It can be, furthermore, that the blow is too strong due to the incorrect insertion, in particular taking into account the incorrect orientation axis, and this causes a crack in the insert and/or the cup that is detrimental to the life span of the prosthesis intended to be inserted into the acetabulum.

The present invention aims to overcome the disadvantages of the prior art by proposing an impaction device which makes it possible for the surgeon impacting an insert into a cup to be sure that, whatever his level of skill on the day, he will apply the correct degree of impact in the correct direction of application such that each time the insert is inserted appropriately into the cup, thus drastically reducing the number of times that the surgeon has to start again repeatedly or use a new insert/cup pair in order to replace the insert/cup pair that has been damaged by a first failed insertion attempt.

According to an aspect of the invention, there is provided an impaction device intended to impart a blow to a stem, in particular a stem that is independent of the device, the stem itself being coupled to an element forming an insert intended to be inserted into a receiving element, in particular a ceramic insert in a cup of a cotyloid cavity of a hip; the impaction device being one as defined by claim 1.

By thus making provision such that the blow is only imparted when the stem/impaction device contact is made perfectly, in particular with sufficient pressure of the device upon the stem, one can be sure that the blow will be applied without any energy loss and along the correct axis, the end of the stem being guaranteed to be located exactly where it must be so that the means of applying a blow administer the blow to it with the intended force and in exactly the right direction, thus drastically reducing applications with a blow of the incorrect value and/or that is out of alignment, in particular one that is weaker than the value that is supposed to be applied in theory. One thus obtains a particularly reliable system that ensures that the surgeon applies a blow to the stem that is as precise as possible and so makes an insertion along the correct axis and with the correct force for the insertion into the cup. On the other hand, the system according to the invention is particularly simple to use, and in particular the cleaning of the system is facilitated by the fact that the stem is independent of the body of the device.

According to one preferred embodiment of the invention, the pre-stressing means are arranged such as to block the action of the means of applying a blow to the stem if the user is not applying the impaction device against the stem with the pre-determined minimum pressure, the arrangement being such that when the pre-determined minimum pressure is applied, the means for applying the blow can be actuated by the triggering means.

According to one beneficial embodiment, the pre-stressing means comprises a runner that is fitted so as to slide relative to the element forming the barrel, the runner being fitted stressed by a spring that keeps the distal end of the runner away from the distal opening of the barrel.

According to one advantageous embodiment, the runner cooperates with the triggering means such that it blocks any action of the triggering means, and when the barrel is pressed against the runner, the latter releases the triggering means.

Preferably, the triggering means comprises a striker controlled by a trigger, the striker hitting the runner in the position in which the device is not exerting any pressure upon the stem with said pre-determined minimum pressure and being released by the runner when at least the pre-determined minimum pressure is being exerted.

According to an improved embodiment, locking means are provided, in particular in the form of a locking ball received in a borehole perpendicular to the axis of the barrel and opening out into the channel that receives the stem, and of a depression formed in the stem, into which the ball penetrates, intended to provide partial limitation of the relative movement of the stem between proximal and distal end positions corresponding to the respective distal and proximal ends of the depression, in the proximal position the stem being in exactly the place where it should be in order to be impacted as intended, and in the distal position the stem being withdrawn from the channel with a large diameter.

According to one preferred embodiment of the invention, means are provided that form a stop originating from the stem intended to strike against the edge of the distal opening of the runner.

The present invention also relates to a unit comprising an impaction device according to the invention and a stem that can be inserted into the receiving channel of the stem that is open at the distal end of the impaction device.

The present invention also relates to a unit comprising an assembly according to the invention and an insert coupled to the stem and a cup in which the insert is intended to be impacted.

By way of example one will now describe a preferred embodiment of the invention, referring to the drawings in which:

FIG. 4A is a top view of the rear side of part of the device of FIG. 2, where the runner and the striker cooperate, in a blocking or safety position of the device;

FIG. 4B is a view identical to FIG. 4A, but in a position that enables the stem to be struck by the hammer, the striker no longer being blocked by the runner;

FIG. 5A is a detailed perspective view of part of FIG. 3A;

FIG. 5B is a perspective view of the proximal end part of the stem inserted into the impaction device in FIG. 5A;

The figures generally show both an impaction device according to an embodiment of the invention and an assembly comprising this impaction device and a stem inserted into the impaction device.

Figure 1:
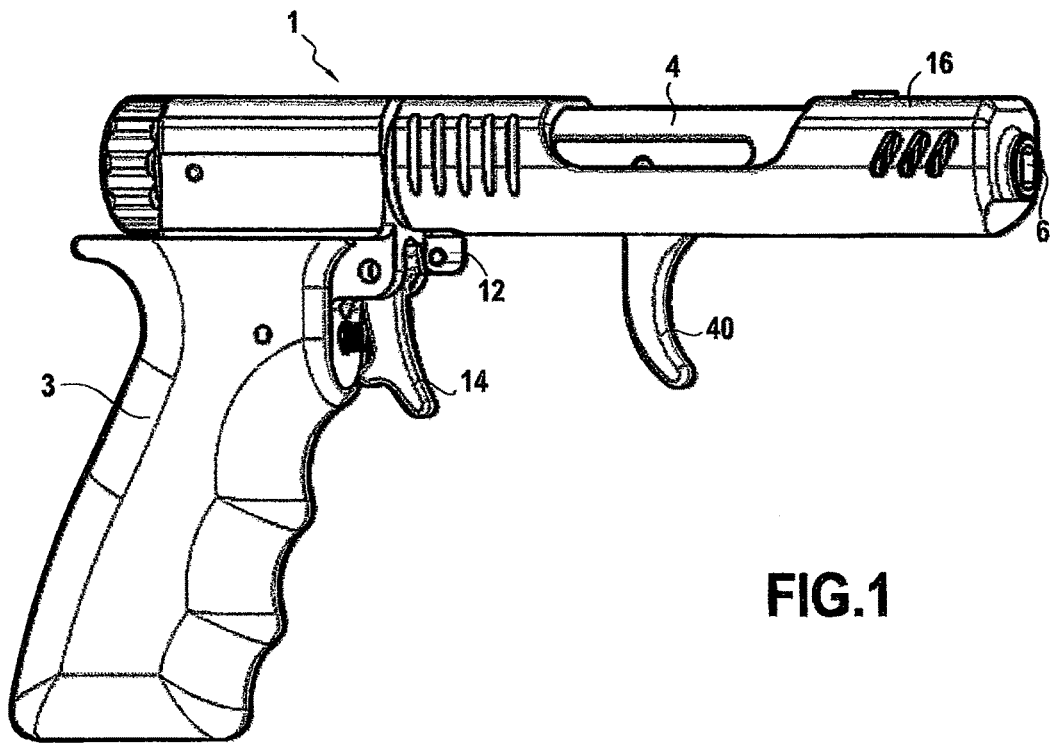
FIG. 1 is a perspective view of an impaction device according to an embodiment of the invention.

FIG. 1 shows the impaction device and a stem according to the invention. The impaction device 1 is in the general form of a pistol. A stem 2 is partially inserted into the barrel of the pistol 1.

The impaction device in the form of a pistol comprises a main body comprising a handle 3 in the form of a pistol grip and a substantially tubular element 4 that forms the barrel extending from the grip. The tubular element 4 forming the barrel defines within it an internal channel 5 that opens out at a distal end opening 6 of the element in the form of a pistol, the stem 2 penetrating via this opening 6.

Figure 6:
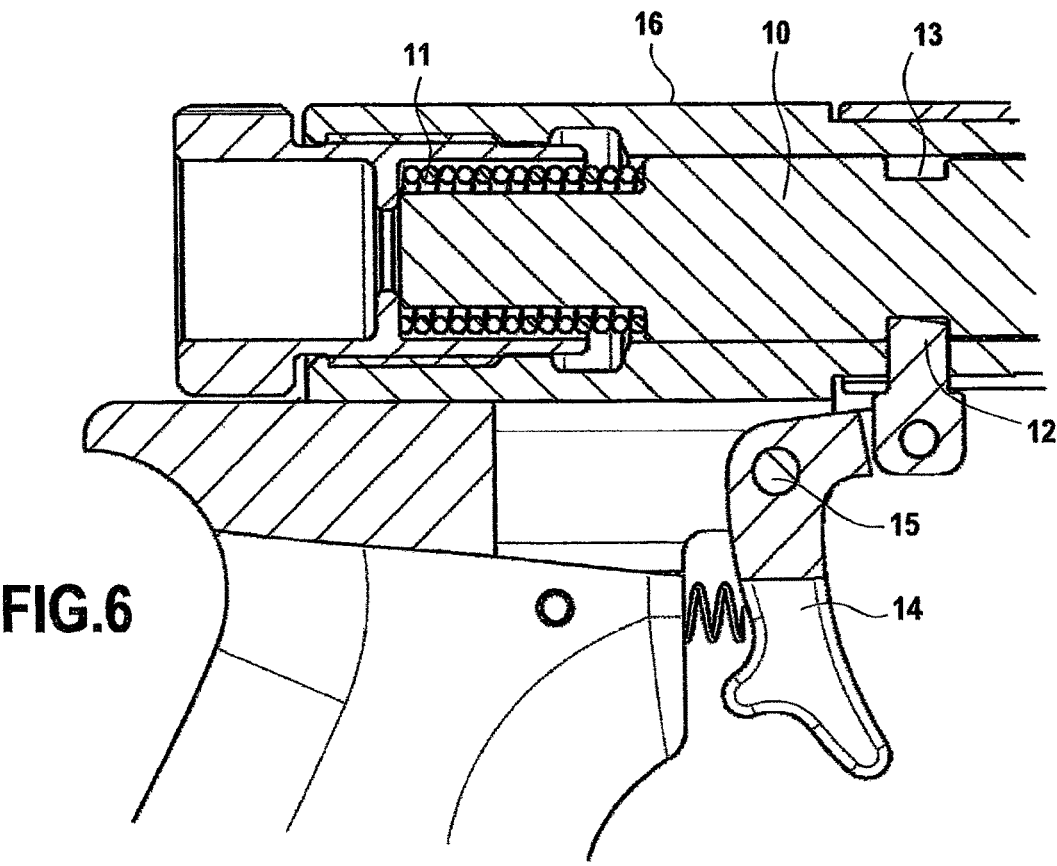
FIG. 6 is a longitudinal sectional view of part of FIG. 2 at the grip, in the blocked position of the striker.
Figure 7:
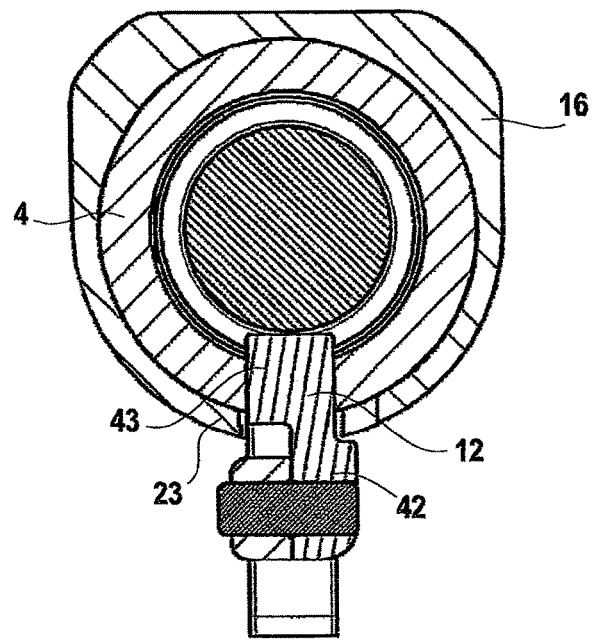
FIG. 7 is a cross-sectional view along line A-A of FIG. 6.

The internal channel 5 comprises a proximal segment 7 with a large cross-section and a distal segment 8 with a smaller section following the segment 7 with a large section, the two segments 7, 8 being separated by a shoulder 9. The small section of the segment 8 is substantially equal to that of the part of the stem 2 intended to be inserted into the pistol and is smaller than the section of the segment 7. There is disposed in the segment 7 a hammer 10 in the form of a cylindrical plunger with a section substantially identical to that of the segment with a large section which is fitted against the bias of a spring 11. The hammer 10 is held against the spring 11 in the compressed state by a spur that forms the striker 12 which penetrates into an annular groove 13 of the hammer. The spur forming the striker 12 comprises a part forming the stem 42 that extends perpendicular to the axis of the barrel and a part forming the head 43 projecting laterally from the stem 42 in order to define a hooking zone, the function of which will be defined further on in the description in connection with a runner 16. A trigger 14 is fitted such as to pivot relative to the grip and is articulated on the stem 42 of the striker 12 such that when the user holds the device by the grip, he can press the trigger 14 with a finger, in particular the index finger, in order to make it pivot in the clockwise direction, in FIG. 6, relative to its axis 15 of rotation (axis perpendicular to the direction of the figure), the effect of this being to make the striker 12 move downwards so that it exits from the groove 13 and releasing the hammer 10 towards the stem (towards the right in FIG. 6) by the effect of the thrust from the released spring 11. The hammer 10 can then strike the proximal end of the stem 2 inserted into the channel 8 and having partially penetrated into the channel 7 with the large section.

The pistol device comprises an element forming the runner 16 in tubular form which surrounds the barrel 4 to a large extent. The runner 16 can slide relative to the barrel 4. At its distal end the runner 16 comprises a distal opening 17 facing the distal opening 6 of the barrel 4 so as to enable the stem 2 to pass within the channel 5 defined in the tubular element 4 forming the barrel.

A helicoidal spring 20 of the runner is fitted within the runner 16, between the runner 16 and the barrel 4. The spring acts on the one hand against the internal lateral distal face 19 of the runner and against an annular stop 21 formed on the external face of the barrel 4, a distance away from the distal opening 6. The spring is arranged such as to keep the internal lateral distal face 19 of the runner and the distal edge of the distal opening 6 of the barrel 4 a distance apart elastically.

The stem 2, which is substantially cylindrical, is shown in detail, as regards a proximal end segment, in FIG. 5B. This proximal segment comprises two opposing left and right flattenings 30 and 31 that have an extension in the longitudinal direction of the stem that is above the longitudinal extension of the segment 8 of the channel 5 with a small diameter. The form of the cross-section of the segment 8 of the channel 5 corresponds to that of the segment of the stem with flattenings, such that when the part of the stem comprising the flattenings is introduced into the channel 5, this can only be done for a given relative orientation of the stem and of the barrel, the flattenings then preventing any rotation of the stem relative to the barrel.

The stem comprises two respective stops 32 at the end of the left and right flattenings 30 and 31 such that the stem can not be introduced any further into the channel 5 when these stops 32 strike against the outer edge of the distal opening of the runner 16.

The stem also comprises two upper and lower depressions 34 formed in the lateral face of the stem 2 extending between the two flattenings.

These two depressions can each receive a locking plunger ball 35 fitted on a spring such as to partially project within the channel segment 8. The ball 35 is fitted in a borehole 50 perpendicular to the axis of the barrel that is biased elastically, for example by a spring (not visible in the figures) which keeps it partially within the segment 8 while, however, being able to be pushed back into the borehole 50 by a thrust action of the stem when it is introduced into the channel so as to allow the passage of the stem, the ball coming back into one of the two depressions, for example the upper depression, after the passage of the proximal part of the stem without a depression.

The relative dimensions of the stem, in particular of the flattenings 30 and 31, of the stops 32, of the depressions 34, of the ball 35, of the segment 8, of the annular stop 21, of the barrel and of the runner are chosen such that on the one hand when the axial stops 32 of the stem strike against the outer edge of the distal opening of the runner 16 and the spring between the runner and the barrel is at rest, the proximal end of the stem does not go past the segment 8 and in particular does not penetrate into the segment 7 with a large section and the ball 35 is partially received in the upper depression 34 and strikes against the proximal edge of the upper depression 34 and on the other hand when the spring is compressed by an action of the user pressing the device, in particular the runner, against the stem such that there is contact between the internal distal face of the runner and the edge of the distal opening of the barrel, the ball strikes against the distal edge of the depression and the stem has penetrated into the channel 7 with a large section, in exactly the correct relative position in relation to the hammer so that the blow is delivered as it should be.

Figure 3A:
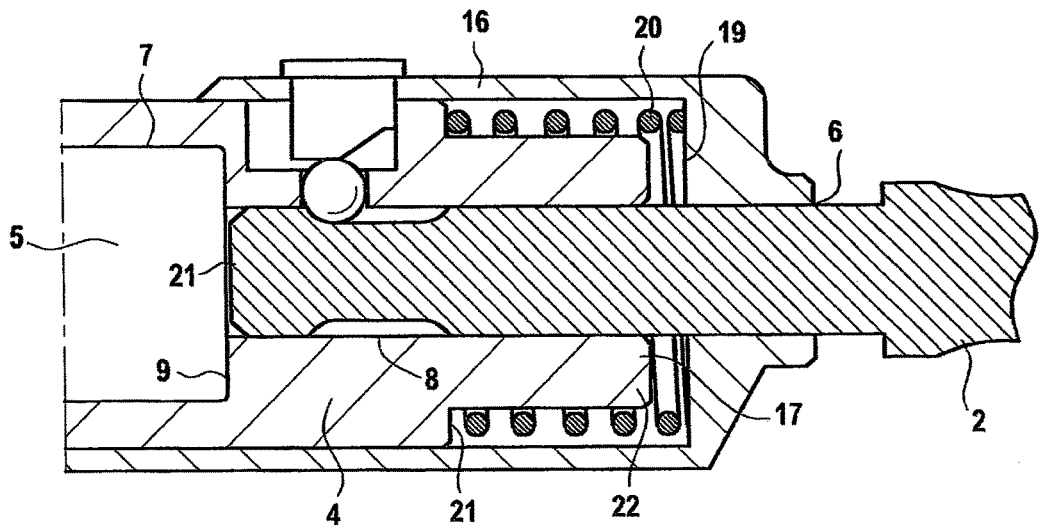
FIG. 3A is a longitudinal sectional view of part of the device of FIG. 2 in a rest position in which the action of the trigger and of the striker is blocked by the runner.
Figure 3B:
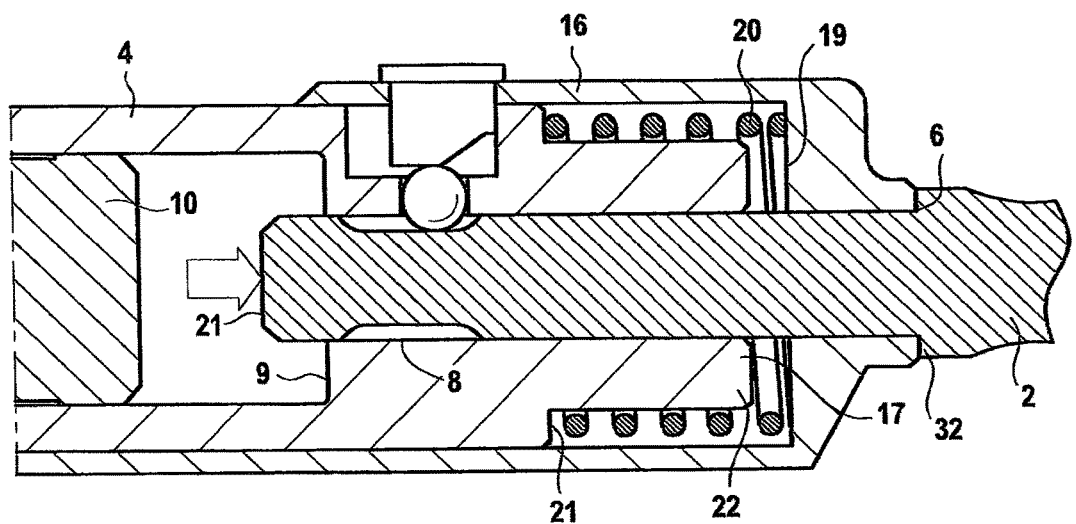
FIG. 3B is a view substantially identical to that of FIG. 3A in a so-called striking position in which the striker is no longer blocked by the runner, such that the hammer can be actuated by pressing the trigger.

The substantially tubular runner 16 is open from the proximal side (see in particular FIGS. 4a and 4b). In a so-called safety position of the device, and in particular in a rest position of the runner spring 20 (FIGS. 3a and 4a), the proximal lateral edge 23 of the runner is hooked by the head 43 of the striker 12, and this prevents any movement of the latter, in particular downwards (towards the top in FIG. 3a).

When the user, having taken the grip in one hand, presses the device against the stem, the effect of this is to make the barrel slide relative to the runner against the compression of the spring 20 until the front end of the barrel comes against the inner lateral wall of the runner, the runner then being shifted relative to the head of the striker (FIG. 4b) and releasing the latter which comes to correspond with a gap formed in the lower part of the runner, the gap being of an appropriate dimension so as to allow it to cross via the head of the striker. The user can then activate the hammer in order to strike the stem which is in the correct position, in particular the proximal end of the stem.

The relative action of the ball and of the depression implements a locking function which enables the user to be informed, when he is pressing the device against the stem, of the position that he is in, in particular at the moment when the striker has been released.

Figure 2:
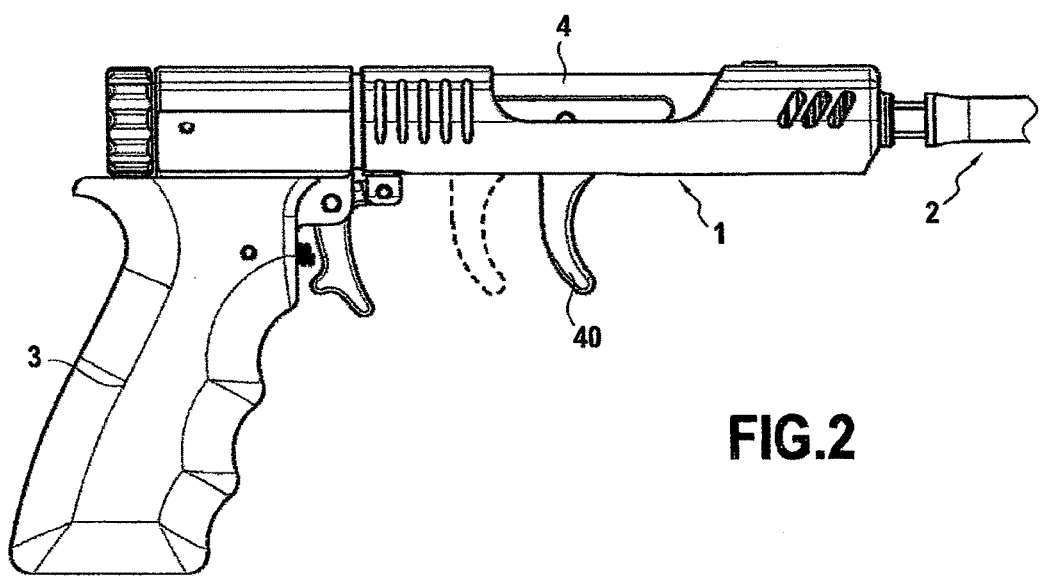
FIG. 2 is a side view in diagrammatic form of the device from FIG. 1, wherein a proximal end segment of the stem intended to receive the impact has been inserted via the open distal end of the impaction device.

A lug 40 is made integrally with the runner 16 and helps the user to slide the runner, in particular against the tension of the spring 20. In FIG. 2 the device is shown in the unarmed or safety position. The position in which the lug 40 is in the armed or unblocked position is shown by dashes. On the other hand, in FIG. 2 the runner is only shown in the safety position.

The invention claimed is:

1. An impaction device (1) intended to impart a blow to a stem, the stem being coupled to an element forming an insert intended to be inserted into a receiving element, in particular a ceramic insert in a cup of a cotyloid cavity of a hip;
   the impaction device (1) comprising
      an element (4) forming a barrel defining a channel (5) that has an opening via which at least part of the stem, in particular a proximal end segment of the stem, can be inserted;
      means (10, 11) of applying a blow intended to apply to the part of the stem introduced into the chamber a pre-determined blow force;
      means (12, 13, 14, 42, 43) for triggering the blow application means, characterized in that pre-stressing means are provided which enable the user to press the device against the stem before triggering the triggering means and so the action of a hammer on the stem, whereas in at least a first blow application position, the proximal end segment of the stem is located at least partially within the channel, and in a second position, after application of the blow, the proximal end segment of the stem is located outside of the channel (5), and whereas the pre-stressing means include a runner (16) having a distal opening with means being provided to form a stop (32) originating from the stem intended to strike against the edge of the distal opening of the runner.

2. The device according to claim 1, characterized in that the pre-stressing means are arranged such as to block the action of the means of applying a blow to the stem if the user is not applying the impaction device against the stem with a pre-determined minimum pressure, whereas when the pre-determined minimum pressure is applied, the means for applying the blow can be actuated by the triggering means.

3. An impacting device (1) intended to impart a blow to a stem, the stem being coupled to an element forming an insert intended to be inserted into a receiving element, in particular a ceramic insert in a cup of a cotyloid cavity of a hip;
   the impaction device (1) comprising
      an element (4) forming a barrel defining a channel (5) that has an opening via which at least part of the stem, in particular a proximal end segment of the stem, can be inserted;
      means (10, 11) of applying a blow intended to apply to the part of the stem introduced into the chamber a pre-determined blow force; and
      means (12, 13, 14, 42, 43) for triggering the blow application means, characterized in that pre-stressing means are provided which enable the user to press the device against the stem before triggering the triggering means and so the action of a hammer on the stem, whereas in at least a first blow application position, the proximal end segment of the stem is located at least partially within the channel, and in a second position, after application of the blow, the proximal end segment of the stem is located outside of the channel (5), the pre-stressing means includes a runner (16) that is fitted so as to slide relative to the element forming the barrel, the runner being stressed by a spring (20) that keeps the distal end of the runner away from the distal opening of the barrel.

4. The device according to claim 3, characterized in that the runner (16) cooperates with the triggering means such that it blocks any action of the triggering means, and when the barrel is pressed against the runner, the runner releases the triggering means.

5. The device according to claim 3, characterized in that the triggering means comprise a striker (12) controlled by a trigger (14), the striker hitting the runner (16) in a position in which the device is not exerting any pressure upon the stem with said pre-determined minimum pressure and being released by the runner when at least the pre-determined minimum pressure is being exerted.

6. The device according to claim 1, characterized in that locking means are provided so as to provide partial limitation of relative movement of the stem between two proximal and distal end positions, in the proximal position the stem being in exactly the place where it should be in order to be impacted as intended, and in the distal position the stem being withdrawn from the channel.

7. An impaction device (1) intended to impart a blow to a stem, the stem being coupled to an element forming an insert intended to be inserted into a receiving element, in particular a ceramic insert in a cup of a cotyloid cavity of a hip;
   the impaction device (1) comprising
      an element (4) forming a barrel defining a channel (5) that has an opening via which at least part of the stem, in particular a proximal end segment of the stem, can be inserted;
      means (10, 11) of applying a blow intended to apply to the part of the stem introduced into the chamber a pre-determined blow force; and
      means (12, 13, 14, 42, 43) for triggering the blow application means, characterized in that pre-stressing means are provided which enable the user to press the device against the stem before triggering the triggering means and so the action of a hammer on the stem, whereas in at least a first blow application position, the proximal end segment of the stem is located at least partially within the channel, and in a second position, after application of the blow, the proximal end segment of the stem is located outside of the channel (5), and locking means are provided so as to provide partial limitation of relative movement of the stem between two proximal and distal end positions, in the proximal position the stem being in exactly the place where it should be in order to be impacted as intended, and in the distal position the stem being withdrawn from the channel, the locking means being in the form of a locking ball (35) received in a borehole (50) perpendicular to the axis of the barrel, and opening out into the channel that receives the stem, and of a depression (34) formed in the stem, into which the ball penetrates, the two proximal and distal end positions corresponding to the respective distal and proximal ends of the depression.

8. A unit comprising an impaction device according to claim 1 and a stem that can be inserted into a receiving channel of the stem that is open at the distal end of the impaction device.

9. An assembly comprising a unit according to claim 8, an insert coupled to the stem and a cup in which the insert is intended to be impacted.

* * * * *